United States Patent [19]

Shiba et al.

[11] Patent Number: 5,318,552
[45] Date of Patent: Jun. 7, 1994

[54] ABSORBENT ARTICLE HAVING AN IMPROVED NON-WOVEN FABRIC LAYER

[75] Inventors: Daisuke Shiba; Akira Yamanoi, both of Utsunomiya, Japan

[73] Assignee: Kao Corporation, Tokyo, Japan

[21] Appl. No.: 849,838

[22] Filed: Mar. 12, 1992

Related U.S. Application Data

[63] Continuation of Ser. No. 485,771, Feb. 26, 1990, abandoned, which is a continuation of Ser. No. 118,952, Nov. 10, 1987, abandoned.

[30] Foreign Application Priority Data

Dec. 10, 1986 [JP] Japan .............................. 61-294425

[51] Int. Cl.$^5$ .............................................. A61F 13/15
[52] U.S. Cl. ...................................... 604/366; 604/376; 604/372
[58] Field of Search ............... 604/366, 365, 376, 372, 604/381

[56] References Cited

U.S. PATENT DOCUMENTS

| | | | |
|---|---|---|---|
| 3,965,906 | 6/1976 | Karami | 604/370 |
| 3,994,299 | 11/1976 | Karami | 604/370 |
| 4,184,902 | 1/1980 | Karami | 604/366 |
| 4,275,105 | 6/1981 | Boyd et al. | 604/366 |
| 4,307,721 | 12/1981 | Tsuchiya et al. | 604/370 |
| 4,392,861 | 7/1983 | Butterworth et al. | 604/366 |
| 4,519,799 | 5/1985 | Sakurai et al. | 604/366 |
| 4,590,114 | 5/1986 | Holtman | 604/370 |
| 4,629,457 | 12/1986 | Ness | 604/370 |
| 4,690,679 | 9/1987 | Mattingly, III et al. | 604/383 |
| 4,767,825 | 8/1988 | Pazos et al. | 604/904 |
| 4,806,598 | 2/1989 | Morman | 604/366 |

*Primary Examiner*—Randall L. Green
*Assistant Examiner*—K. M. Reichle
*Attorney, Agent, or Firm*—Birch, Stewart, Kolasch & Birch

[57] ABSTRACT

An absorbent article comprises as the surface material, a non-woven fabric containing 40 wt. % or more of a conjugate fiber made of a first polyester and a second polyester having a melting temperature of 50° C. or more below that of said first polyester and a height of an endothermic peak of 5% or more of that of the first polyester.

10 Claims, 2 Drawing Sheets

ABSORBENT ARTICLE HAVING AN IMPROVED NON-WOVEN FABRIC LAYER

This application is a continuation of application Ser. No. 07/485,771 filed on Feb. 26, 1990, which is a Rule 62 Continuation Application of Ser. No. 07/118,952 filed on Nov. 10, 1987, both now abandoned, the entire contents of which are incorporated herein by reference.

BACKGROUND OF THE INVENTION

The present invention relates to a disposable absorbent article using a non-woven fabric having excellent absorptivity and processability as the surface material. The present invention particularly relates to an absorbent article such as a sanitary napkin, a paper diaper or a sheet for makeup.

A conventional absorbent article such as a sanitary napkin or a paper diaper basically comprises an absorbent layer made of cottony pulp or absorbent paper, a leakproof layer disposed on the lower and lateral sides of the absorbent layer, and a non-woven fabric provided on the surface of the absorbent layer.

The absorptivity of the absorbent article has been greatly improved in recent years since new materials such as a superabsorbent polymer and a dry process non-woven fabric have been introduced. Particularly as to the non-woven fabric, synthetic fibers have begun to be predominantly used in place of a regenerated fiber of cellulose which has heretofore been widely used. The synthetic fiber is very effective in suppressing the tackiness of the surface of the non-woven fabric.

An absorbent article comprising a combination of materials each having excellent absorptivity cannot be said to sufficiently exhibit the innate performance in actual use. This is apparent from the fact that the consumer's most serious dissatisfaction with an absorbent article such as a sanitary napkin or a paper diaper remains "leakage" from the crotch of a wearer.

The principal causes of leakage are separation of each of the constituent materials and great slippage or wrinkling of the absorbent article due to irregular stresses which are applied to the absorbent article when the crotch of the wearer moves. Among others, particularly the non-woven fabric receives great stress since it is directly in contact with the skin of the wearer so that it is likely to be separated from a waterproof paper layer of an absorbent layer. Thus, integration of the layers by any method is earnestly desired.

As a means of integration of the non-woven fabric with a waterproof paper layer or an absorbent layer, it is conceivable to bond them with a pressure-sensitive adhesive or a hot-melt adhesive. If such a means is employed, the production steps are very complicated, inevitably largely increasing the production cost. In contrast, if a so-called heat bonding method, in which a non-woven fabric is melted and bonded to an object by simple hot-pressing, is employed, the process becomes less complicated, and high-speed production becomes possible with a slight increase in production cost.

In view of the above, a non-woven fabric having good thermal processability is necessary for improving the leakproofness of an absorbent article under conditions of movement of the wearer while not increasing the cost. For high-speed production of such an absorbent article, other excellent processabilities are required of the non-woven fabric in addition to the thermal processability.

The synthetic resin non-woven fabric which has been predominantly used has very insufficient processabilities though it has excellent absorptivity. The problems can be broadly summarized as follows.

A first problem is that thermal processing of the non-woven fabric is difficult. When the non-woven fabric is made of a fiber incapable of being heat-melted, such as an acrylic fiber, the fabric cannot be bonded to an object at all because the non-woven fabric cannot be melted. When a non-woven fabric made of a polyester fiber, a nylon fiber, or the like having a high melting point can be melted by heat, control of the temperature is difficult due to the very high processing temperature, and damage to other materials may be great when the molten non-woven fabric comes in contact with them. Thus, even when the non-woven fabric is melted in processing, the following difficulties are experienced.

The molten fiber sticks to a heat sealer, with the result that the heat-bonded portion of the non-woven fabric is broken and that the function of the sealer is deteriorated because of the resin sticking to the sealer. Even when a low-melting fiber is partially blended in a non-woven fabric in order to lower the processing temperature, the situation is the same as if all of the low-melting fibers are molten. In most cases, the low-melting fiber used herein is one comprising components all having the same melting temperature, such as a polypropylene fiber, or one comprising components having a small difference in melting temperature from one another, such as a polyethylene/polypropylene conjugate fiber. When processing is conducted at a high temperature enough to provide sufficient heat-bonding strength, all components are molten at the same time, and the melted component instantly migrates to the sealer, leading to a reduction in the function of the sealer and to breakage of the heat-bonded portion. As the blending rate of the low-melting fiber is increased, this problem is more serious. When the blending rate of the low-melting fiber is low, migration of the molten component to the sealer can be somewhat prevented by bonding and intertwining of the low-melting fiber with the high-melting fiber in a temperature range wherein all of the low-melting fibers are molten but the high-melting fibers keep the fibrous form. However, the effect of thermal adhesion is hardly exhibited because of the low blending rate of the molten component, and migration of the molten component to the sealer remains yet to be eliminated. Thus, the breakage of the heat-bonded portion of the non-woven fabric and damages caused by the deposited matter accumulated in the sealer by running the sealer particularly for a long period of time cannot be essentially obviated.

There has been an attempt to improve the above-mentioned problems by using as the low-melting fiber a polyester/polyester conjugate fiber having a large difference in the melting temperature between the two components of the fibers. In this case, a conventional low-melting polyester component is so amorphous that it does not have a melting temperature (but has a softening point) in a strict sense. Thus, adhesion to another object is low and hence an insufficient sealing strength can be obtained even at a temperature above the softening point.

As described above, thermal processing of a non-woven fabric based on a synthetic fiber can merely be conducted in a very restricted range. Particularly, it is impossible to conduct thermal processing which will exert a consistent effect on a non-woven fabric having a very high blending rate of a low-melting fiber used as the binder, such as a dry process heat-bonded non-woven fabric which is widely used in absorbent articles.

Thus, in the most widely employed method of providing thermal processability to a synthetic fiber-based non-woven fabric, a polyolefin fiber or its conjugate fiber having a relatively high bonding strength when thermally processed is blended within a range wherein the fiber does not fuse as much to a sealer. However, this method can not essentially solve the above-mentioned problem, and involves the following serious problem.

Specifically, a second problem is that when a polyolefin fiber is used, the cuttability of a non-woven fabric is lessened. In production of a disposable absorbent article such as a sanitary napkin or a paper diaper, the step of cutting a product or a raw material does not fail to be included in the process. Generally speaking, the cuttability of a synthetic fiber is poor when compared with a regenerated cellulose fiber such as rayon. A high-speed productivity is required with the above-mentioned absorbent article for lowering the cost. Thus, cutting must be done in a very short time and the cutting system is limited. In a cutting system using a metal blade, which is usually employed, the durability of the blade is greatly affected by the properties of the materials such as a non-woven fabric. On the non-woven fabric side, the fabric should not undergo damages to a portion other than the cut portion It is believed that the cuttability has something to do with the viscoelasticity of the fibers. The cuttability of a polyolefin fiber having a high viscoelasticity is particularly poor, while those of a polyester fiber or an acrylic fiber having higher brittleness are relatively good. Accordingly, a dry process heat-bonded non-woven fabric based on a polyolefin fiber and a non-woven fabric containing a polyolefin fiber blended for providing thermal processability is difficult to process. Thus, difficulty is encountered in high-speed production of an absorbent article.

As described above, a conventional non-woven fabric based on a synthetic fiber does not simultaneously satisfy sufficient thermal processability and cuttability under conditions of high-speed production. Thus, an absorbent article which hardly slips or wrinkles and has a high leakproofness has not been obtained.

SUMMARY OF THE INVENTION

The inventors of the present invention have made intensive investigations with a view to providing a non-woven fabric having sufficient thermal processability and cuttability, high strength and absorptivity, and good handling. As a result, they have completed the absorbent article of the present invention.

Specifically, the present invention provides an absorbent article comprising, as the surface material, a non-woven fabric containing 40 wt. % or more of a conjugate fiber made of a first polyester and a second polyester having a melting temperature of 50° C. or more below that of said first polyester and a height of an endothermic peak of 5% or more of the first polyester.

When the first problem as summarized hereinabove is considered, the non-woven fabric to be used in the absorbent article of the present invention must satisfy at least the following conditions in thermal processing.

A first condition is that at least part of the non-woven fabric is molten and efficiently bonded to an object under heat and pressure. This is obvious when the purpose of the invention is considered. A second condition is that the component of the non-woven fabric molten under heat and pressure does not migrate to a sealer. A third condition is that the above-mentioned conditions can be satisfied in a wide temperature range. Particularly, the second and third conditions are quite important requisites in conducting stable thermal processing in actual production.

As a result of the investigation on these conditions, the inventors of the present invention have found that a non-woven fabric satisfying the above-mentioned conditions can be obtained by the following method.

First, in order to improve the efficiency of bonding of the non-woven fabric to an object, a component which not only is molten under heat and pressure, but also rapidly flows to reach the object after melting must be included in the non-woven fabric. The second polyester in the conjugate fiber according to the present invention corresponds to this component.

Second, the method of preventing migration of the component of the non-woven fabric to a sealer and breakage of the bonded portion will be described. This is attained by using a fiber wherein not all the resin components are molten under heat and pressure. Specifically, the second polyester is molten with adequate flowability at the time of heat bonding, while the first polyester is not molten and maintains the form of the fiber to serve as a skeleton of the non-woven fabric. A conjugate fiber as mentioned just above should be used for attaining the purpose. In order to certainly realize such an effect within a range of dispersion of the heat bonding temperature and the line in actual production, a difference in melting temperature between the first and second polyesters must be at least 50° C., desirably 100° C. or more. In such a conjugate fiber, as the melting temperature of the first polyester is higher, the thermal processing can be done in a wider temperature range.

In order that the non-woven fabric simultaneously satisfies the first and second conditions necessary with regard to thermal processability, the above-mentioned conjugate fiber made of the first and second polyesters must be partially contained at least in the surface layer of the non-woven fabric. As the blending rate of the conjugate fiber in the surface layer is increased, the adhesion strength increases without breakage of the heat-bonded portion and fusion of the resin to the sealer, thus improving the thermal processability of the non-woven fabric.

In order that the non-woven fabric according to the present invention satisfies the third condition necessary for thermal processing, it is desired that the bonding by thermal processing occurs at as low a temperature as possible while fusion to the sealer does not occur up to as high a temperature as possible. Namely, it is desired that the first polyester of the conjugate fiber according to the present invention has as high a melting temperature as possible, while the second polyester has as low a melting temperature as possible. The melting temperature of the first polyester is desirably 200° C. or higher, while that of the second polyester is desirably 180° C. or lower.

When attention is paid only to the thermal processability, examples of the conjugate fiber (first resin component/second resin component) satisfying the above-mentioned properties include polypropylene/low density polyethylene, polypropylene/ethylene-vinyl acetate copolymer, polyester/polyethylene, and polyester/amorphous polyester. Among them, conventional polyester/amorphous polyester provides such a poor bonding to an object that no sufficient sealing strength can be obtained, because the polyester as the second resin component has a low thermal flowability due to amorphousness.

The cuttability of the non-woven fabric as the second problem summarized hereinabove is considered in addition to the thermal processability. The above-mentioned polyolefin-based conjugate fibers having good thermal processability have poor cuttability of a non-woven fabric as discussed above. The conventional polyester/amorphous polyester conjugate fiber has relatively good cuttability in contrast with thermal processability.

The inventors of the present invention, based on the overall consideration of the above, have attempted to modify the polyester/amorphous polyester conjugate fiber to improve the thermal processability thereof. As a result, it has become possible to prepare a non-woven fabric which has good thermal processability comparable to those of polyolefin-based conjugate fibers without detriment to the cuttability and which has excellent strength and handling which cannot be obtained by the conventional polyester/amorphous polyester conjugate fiber.

The aim of the modification is to impart adequate thermal flowability, bonding strength after heat melting and adequate melting temperature to the conventional amorphous polyester component. These physical properties have a complicated correlation with the molecular structure of the resin and the crystalline structure in a fibrous form. The inventors of the present invention have focused their attention mainly on the molecular weight of the resin component, the crystallinity in the fibrous form, and the like, and controlled them to realize the desired modification. They have found that the endothermic peak of the low-melting polyester component when molten by heat corresponds to flowability and bonding strength, and hence can serve as an index therefor. Specifically, it has been found that, when the molecular weight, crystallinity in the fibrous form, or the like of the second polyester are controlled to be increased in such a way as will increase the proportion of an endothermic peak of the second polyester when molten by heat relative to an endothermic peak of the first polyester, the flowability at the time of melting by heat and heat bonding strength are increased. In fact, the conventional amorphous polyester, which is poor in flowability when molten by heat and heat-bonding strength, has no melting temperature and a proportion of an endothermic peak thereof as mentioned above is 0%. In order to satisfy the above-mentioned three conditions necessary for thermal processing of the non-woven fabric, the height of the endothermic peak of the second polyester must be 5% or more, desirably 20% or more, of that of the first polyester.

Any polyester resin having a high melting temperature and good cuttability may be used as the first polyester. Examples of the first polyester resin include not only the most common polyethylene terephthalate but also polybutylene terephthalate. The melting temperature of the second polyester must be designed to be at least 50° C., desirably at least 100° C., lower than that of the first polyester.

A non-woven fabric having excellent heat processability and cuttability is formed from a conjugate fiber (hereinafter referred to as "PET/lmpPET", i.e., polyethylene terephthalate/low melting point polyethylene terephthalate) by the following procedure. Specifically, when the cuttablity of a fiber other than PET/lmpPET is good as in the case of a polyester fiber and an acrylic fiber, only good thermal processability must be imparted to the non-woven fabric constituted of that fiber. When the cuttability of a fiber other than PET/lmpPET is not good as in the case of a polyolefin fiber, the cuttability of such a fiber may be improved by blending PET/lmpPET in a non-woven fabric constituted of such a fiber.

In any case, inclusion of PET/lmpPET at least in every layer of the non-woven fabric is necessary. In order to secure a consistent effect, PET/lmpPET must be contained in an amount of 40 wt. % or more on the average in the non-woven fabric.

Besides the above-mentioned results, the PET/lmpPET according to the present invention enables production of a non-woven fabric having excellent strength and handling which cannot be obtained from the conventional polyester/amorphous polyester conjugate fiber.

Conditions for most effectively using the conjugate fiber according to the present invention in a dry process heat bonded non-woven fabric will now be described.

When consideration is given to the balance of the strength and handling of a non-woven fabric itself, at least the surface layer of the non-woven fabric comprises a conjugate fiber according to the present invention and a fiber having a melting temperature comparable to or higher than that of a second polyester of the conjugate fiber in an aspect of a composition. The average weight proportion of them is desirably in the range of 40 to 100:60 to 0. The areal weight is desired to be 10 to 40 g/m² for overall and 5 to 15 g/m² for the surface layer in the case of use in a sanitary napkin, and 20 to 50 g/m² for overall and 7 to 20 g/m² in the case of use in a paper diaper. Particularly in order to obtain strength and handling comparable to those of a non-woven fabric based on a polyolefin fiber, the melt viscosity of the second polyester as the direct index of flowability is 5 poises or lower at 200° C. The fineness of the conjugate fiber according to the present invention may be 1.5 to 10 deniers. It is preferably 1.5 to 6 deniers when consideration is given to the strength and handling.

Lastly, in order that an absorbent article has an adequate absorptivity, an adequate hydrophilic nature is preferably imparted to a non-woven fabric. Thus, the conjugate fiber according to the present invention is desired to have a hydrophilic nature at least on its surface. Methods of making the surface hydrophilic include one in which the surface of the conjugate fiber is treated with a surfactant to make it hydrophilic, one in which a chemical substance having a hydrophilic group, such as a monomer having a hydrophilic group or a polymer having a hydrophilic group, is chemically bonded to the conjugate fiber to effect chemical surface modification, one using plasma processing, and one in which a chemical substance having a hydrophilic group is kneaded into the conjugate fiber to effect physical surface modification. In chemical surface modification, a chemical substance having a hydrophilic group may be chemically bonded to the fiber surface, or a chemical substance having a hydrophilic group may be bonded and crosslinked between the molecules thereof to cover the fiber surface. As described above, the methods of making the fiber hydrophilic during the fiber production step are generally employed. Alternatively, a non-woven fabric is formed and then post-treated to effect the above-mentioned chemical or physical surface modification, or the treatment with a surfactant, whereby the hydrophilic nature may be imparted to the surface of the conjugate fiber according to the present inveniton.

DESCRIPTION OF THE PREFERRED EMBODIMENTS

Absorbent articles thermally processed using a non-woven fabric according to the present invention will now be described in more detail with reference to Examples.

EXAMPLES 1 to 11 and COMPARATIVE EXAMPLES 1 to 8

Fibers used as conjugate fibers according to the present invention and fibers used as ones outside the scope of the present invention are summarized in Table 1.

Physical properties of non-woven fabrics prepared using these fibers and absorbent articles of the present invention and comparative absorbent articles using these non-woven fabrics are summarized in Table 2.

In Examples 1 to 5, Examples 9 to 11, Comparative Examples 1 to 3, and Comparative Examples 6 to 8, a non-woven fabric was prepared by the heat bonding method using a conjugated fiber as the binder fiber (hot air of 140° C. was passed through a card web to fuse the conjugated fiber to other fiber, thereby effecting fixation). In Examples 6 to 8 and Comparative Examples 4 and 5, a non-woven fabric was formed by ejecting a high-pressure water flow (propellent pressure: 55 kg/cm$^2$) against a card web .to intertwine fibers.

An absorbent article was produced by placing a non-woven fabric as mentioned in Table 2 instead of a non-woven fabric removed from a commercially available sanitary napkin (trade name: Lorie Safety Long (manufactured by Kao Soap Co., Ltd. )). Sealing and cutting operations were conducted as follows.

Referring now to the numbers 1 is a test piece, 2 is a sealed portion, 3 is a non-woven fabric, 4 is a laminated paper, 5 is a chuck, 6 is a movable female waist model, 7 is a measurement sample, 8 is a tube, 9 is a surface layer of a non-woven fabric, 10 are conjugate fibers, 11 is an absorbent member and 12 is a leakproof sheet.

Testing Method of Fiber and Non-Woven Fabric

Regarding the fibers shown in Table 1, the melting temperatures of the first and second resin components were measured by the following method, and the proportion of the height of an endothermic peak of the second resin component relative to that of an endothermic peak of the first resin component was calculated by the following method.

Among the items of Table 2, the tensile strength was measured as to a non-woven fabric by the following method, while the bonding strength and bonding state are measured by the following method after the non-woven fabric and a leakproof sheet were subjected to the following sealing operation. The same sealing operation was made as to the absorbent article to integrate the non-woven fabric and the leakproof sheet, and the amount of dynamic absorption was measured by the following method.

(1) Melting temperature

As to the fibers as mentioned in Table 1, it is measured by the following method. The temperature of the endothermic peak observed when a sample is heated up at a rate of 10° C./min using DSC, i.e. Differential Scanning Colorimetry is defined as the melting temperature.

(2) Proportion of endothermic peak of second resin component relative to that of first resin component When the height of the endothermic peak of the first resin component is $H_1$ and the height of the endothermic peak of the second resin component is $H_2$, these values are read from a DSC chart, and the above-mentioned proportion is calculated by the equation $(H_2/H_1) \times 100$ (%).

(3) Tensile strength

A non-woven fabric having a width of 50 mm and a length of 150 mm is pinched and pulled at a pulling rate of 300 m/min. The breaking strength is defined as the value of tensile strength. The fiber orientation of the non-woven fabric is in the width direction of the non-woven fabric sample.

(4) Sealing operation

As to absorbent articles as shown in Table 2, a non-woven fabric and a leakproof sheet (modified polyethylene-laminated paper) are heat-sealed with a sealing width of 2 mm at a line speed of 30 m/min.

(5) Bonding strength

Figure 1:
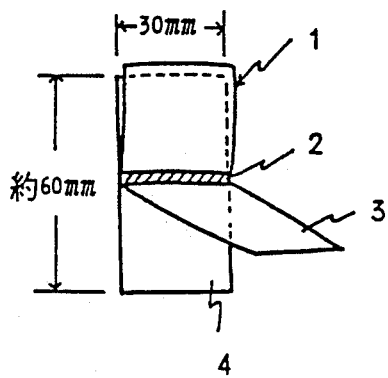
FIG. 1 is a perspective view of a sample for measurement of the bonding strength.
Figure 2:
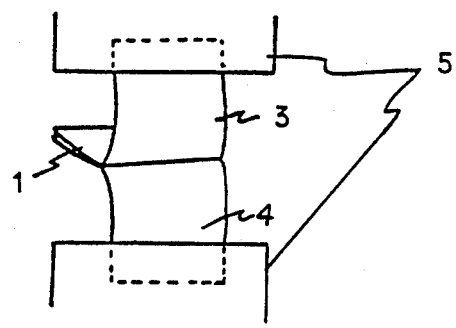
FIG. 2 is a perspective view thereof under measurement.

A test piece 1 as shown in FIG. 1 which includes a sealing portion 2 and has a width of 30 mm is cut from a sample after the sealing test. As shown in FIG. 2, the end portion of the non-woven fabric 3 and the end portion of the laminated paper 4 are respectively pinched by chucks 5 and pulled. The maximum peeling load is defined as the bonding strength.

(6) Bonding state

A sealing portion is visually observed to evaluate the bonding state. The rating criteria are as follows. Third grade ... There is neither breakage in a heat bonded portion nor adhesion to a sealer. Second grade ... There is a partial breakage or incomplete bonding but no adhesion to the sealer. First grade ... There are breakage in a heat-bonded portion and adhesion to the sealer. Thus, heat bonding is impossible.

(7) Amount of dynamic absorption

Figure 3:
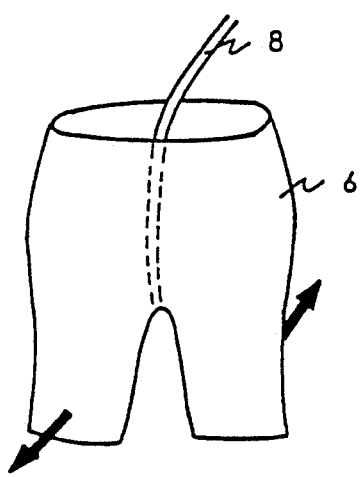
FIG. 3 is a perspective view of a movable female waist model for measurement of the amount dynamic adsorption.
Figure 4:
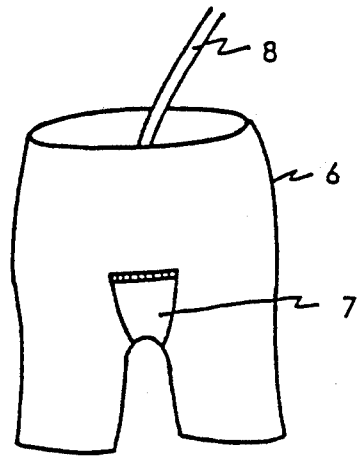
FIG. 4 is a view showing a sample worn on the movable female waist model.
Figure 5:
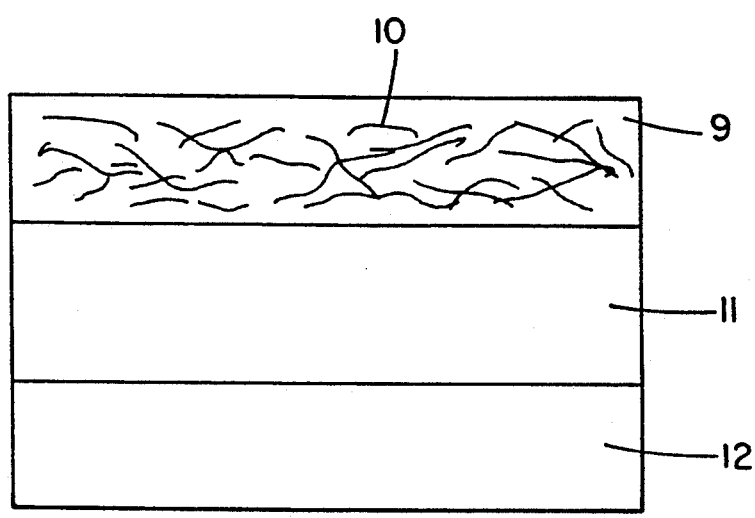
FIG. 5 is a cross-sectional view of an absorbent article.

A measurement sample 7 is put on a movable female waist model 6 as shown in FIG. 3 in such a way as shown in FIG. 4. After it is started, a test liquid is injected through a tube 8 into the sample at a rate of 15 g/min while continuing walking movement. The amount of the test liquid injected when leakage is confirmed is defined as the amount of dynamic absorption. The larger the amount of dynamic absorption, the less liable to occur the leakage.

(8) Cuttability

An absorbent article subjected to the sealing operation is cut with a rotary die cutter while passing it at a line speed of 30 m/min to evaluate the cuttability. The rating criteria are as follows. Third grade ... The cut portion is completely cut. Second grade ... Part of the cut portion remains uncut. First grade ... The portion to be cut is hardly cut.

TABLE 1

| Fiber | Ref. No. | Maker | First resin component Composition | Melting Temp. °C. | Second resin component Composition | Melting Temp. °C. | Proportion of height of endothermic peak of second resin relative to that of first resin |
|---|---|---|---|---|---|---|---|
| PET-1 | PET-1 | Teijin | Polyethylene terephthalate | 251 | Low-crystallinity polyester | 133 | 5 |
| PET-2 | PET-2 | Teijin | Polyethylene terephthalate | 255 | Low-crystallinity polyester | 129 | 9 |
| PET-3 | PET-3 | Teijin | Polyethylene terephthalate | 256 | Low-crystallinity polyester | 132 | 18 |
| PET-4 | PET-4 | Teijin | Polyethylene terephthalate | 250 | Low-crystallinity polyester | 134 | 39 |
| PET-5 | PET-5 | Teijin | Polyethylene terephthalate | 251 | Low-crystallinity polyester | 134 | 55 |
| PET-6 | PET-6 | Teijin | Polyethylene terephthalate | 255 | Low-crystallinity polyester | 133 | 7 |
| Melty | PET-7 | Unitika | Polyethylene terephthalate | 255 | Amorphous polyester | No peak observed | 0 |
| NBF(SH) | SH | Daiwa Spinning | Polyester | 265 | Polyethylene | 133 | 212 |
| NBF(H) | NBH | Daiwa Spinning | Polypropylene | 161 | Polyethylene | 133 | 262 |
| PP | PP | Daiwa Spinning | Polypropylene | 163 | | | |
| PET | PET | Teijin | Polyethylene terephthalate | 268 | | | |

(Note) Low-crystallinity polyester and amorphous polyester are made of polyethylene terephthalate.

TABLE 2

| Ex. No. and Comp. Ex. No. | Web stabilization method | Areal weight g/m² | Non-woven fabric Surface layer Areal weight g/m² | Fiber | Fineness denier | Mixing rate % | Reverse layer Areal weight g/m² | Fiber | Fineness denier | Mixing rate % |
|---|---|---|---|---|---|---|---|---|---|---|
| Ex. 1 | heat bonding | 27 | 12 | PET-1 | 3 | 100 | 15 | PET-1 / PET | 3 / 6 | 50 / 50 |
| Ex. 2 | heat bonding | 27 | 12 | PET-2 | 3 | 100 | 15 | PET-2 / PET | 3 / 6 | 50 / 50 |
| Ex. 3 | heat bonding | 27 | 12 | PET-3 | 3 | 100 | 15 | PET-3 / PET | 3 / 6 | 50 / 50 |
| Ex. 4 | heat bonding | 27 | 12 | PET-4 | 3 | 100 | 15 | PET-4 / PET | 3 / 6 | 50 / 50 |
| Ex. 5 | heat bonding | 27 | 12 | PET-5 | 3 | 100 | 15 | PET-5 / PET | 3 / 6 | 50 / 50 |
| Comp. Ex. 1 | heat bonding | 27 | 12 | PET-7 | 4 | 100 | 15 | PET-7 / PET | 4 / 6 | 50 / 50 |
| Comp. Ex. 2 | heat bonding | 27 | 12 | SH | 2 | 100 | 15 | SH / PET | 2 / 6 | 50 / 50 |
| Comp. Ex. 3 | heat bonding | 27 | 12 | NBH | 2 | 100 | 15 | NBH / PET | 2 / 6 | 50 / 50 |
| Comp. Ex. 4 | fluid interlocking | 40 | | PET-5 / PET | 3 / 2 | 0 / 100 | | | | |
| Comp. Ex. 5 | fluid interlocking | 40 | | PET-5 / PET | 3 / 2 | 25 / 72 | | | | |
| Ex. 6 | fluid interlocking | 40 | | PET-5 / PET | 3 / 2 | 40 / 60 | | | | |
| Ex. 7 | fluid interlocking | 40 | | PET-5 / PET | 3 / 2 | 80 / 20 | | | | |
| Ex. 8 | fluid interlocking | 40 | | PET-5 / PET | 3 / 2 | 100 / 0 | | | | |
| Comp. Ex. 6 | heat bonding | 27 | | PET-5 / SH | 3 / 2 | 0 / 100 | | | | |
| Comp. Ex. 7 | heat bonding | 27 | | PET-5 / SH | 3 / 2 | 3 / 70 | | | | |
| Ex. 9 | heat bonding | 27 | | PET-5 / SH | 3 / 2 | 40 / 60 | | | | |

TABLE 2-continued

| Ex. 10 | heat bonding | 27 | 12 | PET-5 SH | 3 2 | 70 30 | | | | |
|---|---|---|---|---|---|---|---|---|---|---|
| Comp. Ex. 8 | heat bonding | 27 | 12 | PET-5 | 3 | 100 | 15 | PP | 2 | 100 |
| Ex. 11 | heat bonding | 27 | 12 | PET-5 | 3 | 100 | 15 | PP PET-5 | 2 3 | 70 30 |

| | Absorbent article | | | | | |
|---|---|---|---|---|---|---|
| Ex. No. and Comp. Ex. No. | Tensile strength g/50 mm | Bonding strength g/30 mm | Bonding state grade | Amount of dynamic absorption g | Processing temp. °C. | Cuttability grade |
| Ex. 1 | 125 | 101 | 3 | 7.6 | 220 | 3 |
| Ex. 2 | 149 | 120 | 3 | 8.1 | 220 | 3 |
| Ex. 3 | 192 | 155 | 3 | 9.1 | 220 | 3 |
| Ex. 4 | 223 | 188 | 3 | 8.0 | 220 | 3 |
| Ex. 5 | 268 | 203 | 3 | 8.0 | 220 | 3 |
| Comp. Ex. 1 | 66 | 35 | 2 | 5.1 | 220 | 3 |
| Comp. Ex. 2 | 301 | 156 | 3 | 7.8 | 220 | 1 |
| Comp. Ex. 3 | 330 | 99 | 2 | 6.4 | 160 | 1 |
| Comp. Ex. 4 | 220 | 0 | not bonding | 4.3 | 220 | 3 |
| Comp. Ex. 5 | 206 | 39 | 3 | 4.6 | 220 | 3 |
| Ex. 6 | 232 | 75 | 3 | 7.0 | 220 | 3 |
| Ex. 7 | 222 | 201 | 3 | 9.5 | 220 | 3 |
| Ex. 8 | 229 | 255 | 3 | 8.3 | 220 | 3 |
| Comp. Ex. 6 | 201 | 231 | 3 | 8.8 | 220 | 1 |
| Comp. Ex. 7 | 215 | 222 | 3 | 7.6 | 220 | 2 |
| Ex. 9 | 213 | 212 | 3 | 8.1 | 220 | 3 |
| Ex. 10 | 241 | 219 | 3 | 8.2 | 220 | 3 |
| Comp. Ex. 8 | 235 | 226 | 3 | 8.2 | 220 | 1 |
| Ex. 11 | 241 | 234 | 3 | 7.9 | 220 | 3 |

As is apparent from Examples 1 to 12, the non-woven fabric according to the present invention provides a high bonding strength and a good bonding state when thermally processed, and has very good cuttability. The absorbent article obtained by integrating the non-woven fabric and the leakproof layer by heat bonding shows a large amount of dynamic absorption.

In Comparative Example 1, since the proportion of an endothermic peak of a second resin component, PET-7, relative to that of a first resin component is 0%, the bonding strength by thermal processing is poor, the amount of dynamic absorption of the absorbent article is small, and the strength of the non-woven fabric is poor.

Comparative Examples 2 and 3 are good in thermal processing, but the cuttability is so poor that high-speed production may be impossible, since the second resin component is a polyolefin.

Comparative Examples 4 and 5 have a good cuttability but their bonding strength is unpractically low because the blending ratio of PET to impPET according to the present invention is low.

Comparative Examples 6 and 7 have a good thermal processability but a poor cuttability in contrast with Examples 4 and 5 because the blending rate of PET to lmpPET according to the present invention is small and a polyolefin fiber is mainly used.

Comparative Example 8 has a poor cuttability because the content of polyolefin, PP, is 100% in the reverse surface layer.

What is claimed is:

1. In an absorbent article having an absorbent member, a leakproof layer, and a non-woven fabric layer comprising at least a surface layer, the improvement comprising said non-woven fabric being 40 wt % or more of conjugate fibers, each of said conjugate fibers being made of a first polyester and a second low crystalline polyester, said second low crystalline polyester (1) having a melting temperature of 50° C. or more below the melting temperature of said first polyester, and (2) a height of an endothermic peak of 5% or greater, as measured by Differential Scanning Colorimetry, than that of said first polyester, said conjugate fibers being contained in every layer of said non-woven fabric layer.

2. The absorbent article of claim 1 wherein said conjugate fibers are further treated with a surfactant.

3. The absorbent article of claim 1 wherein said conjugate fibers are further treated with a substance having a hydrophilic group and is chemically bonded to said conjugate fibers.

4. The absorbent article of claim 1 wherein said conjugate fibers are further treated with a chemical substance having a hydrophilic group which is kneaded into said conjugate fibers.

5. The absorbent article of claim 1 wherein the thickness of said conjugate fibers is from 1.5 to 10 deniers.

6. The absorbent article of claim 1 wherein said second polyester has a melting temperature of at least 100° C. below the melting temperature of said first polyester.

7. The absorbent article according to claim 1, wherein said non-woven fabric is heat bonded to said leakproof layer.

8. The absorbent article according to claim 1, wherein said conjugate fibers are made hydrophilic by plasma processing.

9. The absorbent article according to claim 1, wherein said height of endothermic peak of said second polyester is 20% or greater, as measured by Differential Scanning Colorimetry, than that of said first polyester.

10. The absorbent article according to claim 1, wherein said second polyester is a low melting point polyethylene terephthalate.

* * * * *